(12) United States Patent
Kumar

(10) Patent No.: US 6,808,918 B2
(45) Date of Patent: Oct. 26, 2004

(54) PRODUCTION OF ASCORBIC ACID

(75) Inventor: Manoj Kumar, Fremont, CA (US)

(73) Assignee: Genencor International, Inc., Palo Alto, CA (US)

( * ) Notice: Subject to any disclaimer, the term of this patent is extended or adjusted under 35 U.S.C. 154(b) by 85 days.

(21) Appl. No.: 10/026,586

(22) Filed: Dec. 18, 2001

(65) Prior Publication Data

US 2002/0076771 A1 Jun. 20, 2002

Related U.S. Application Data

(62) Division of application No. 09/205,874, filed on Dec. 4, 1998, now Pat. No. 6,358,715.

(51) Int. Cl.[7] ............................. C12N 1/14; C12N 1/16; C12N 9/00; C12N 9/02; C07H 21/04

(52) U.S. Cl. ............................ 435/255.4; 435/4; 435/6; 435/25; 435/29; 435/69.1; 435/41; 435/135 T; 435/183 T; 435/189 T; 435/252.3; 435/255.1; 435/255.3; 435/320.1; 435/262; 536/23.2 T

(58) Field of Search ........................... 435/4, 6, 25, 29, 435/69.1, 41, 135 T, 183, 189, 252.3, 255.1, 255.3, 255.4, 320.1, 262, 254.1, 254.11, 254.2, 254.21, 138, 136, 183 T, 41 T, 135; 536/23.2 T

(56) References Cited

U.S. PATENT DOCUMENTS

| | | | |
|---|---|---|---|
| 4,595,659 A | | 6/1986 | Roland et al. |
| 4,757,012 A | | 7/1988 | Estell et al. |
| 4,758,514 A | | 7/1988 | Light et al. |
| 4,916,068 A | | 4/1990 | Roland et al. |
| 4,945,052 A | * | 7/1990 | Hardy et al. ............. 435/172.3 |
| 5,004,690 A | | 4/1991 | Light et al. |
| 5,032,514 A | | 7/1991 | Anderson et al. |

FOREIGN PATENT DOCUMENTS

| | | |
|---|---|---|
| WO | WO 85/01745 | 4/1985 |
| WO | WO 87/00863 A | 2/1987 |
| WO | WO 96/12846 | 5/1996 |

OTHER PUBLICATIONS

*Bleeg, "L–Ascorbic Acid in Yeast and Isolation of L–Galactono–Lactone Oxidase from the Mitochandria", *Enzymologia acta biocatalytica*, Uitgeverij Dr. W. Junk—Den Haag, 1966 pp. 105–112.

*Bleeg, "Biosynthesis of Ascorbate in Yeast", *Eur. J. Biochem*, 127, 391–396 (9182) FEBS 1982.

*Bunton et al., "The Determination of Ascorbic and Erythorbic Acids in Meat Products", *J. Assoc. Publ. Analysts*, 1979, 17, 105,–110.

*Chemical Abstract V. 84 (5), Feb. 2, 1976, Columbus Ohio, US, Abstract No. 29189, Obata, Yasuo et al: L–Ascorbic acid XP002135678 abstract and JP 50 022113 b (Takeda Chemical Industries, Ltd., Japan) Jul. 28, 1975.

*Costamagna et al., "Ascorbic acid specific utilization by some yeasts", *Can. J. Microbiol.* vol. 32, Jun. 12, 1986, pp 756–758.

*Frey et al., "The Molecular Biology of Inc Q Plasmids", *Replication Proteins of the IncQ Plasmid RSF1010*, pp 79–94.

*Frey et al., "Replication and copy number control of the broad–host–range plasmid RSF1010", *Gene*, 113 (1992) 101–106.

(List continued on next page.)

Primary Examiner—Manjunath N. Rao
(74) Attorney, Agent, or Firm—Genencor International, Inc.

(57) ABSTRACT

The present invention provides for the production of ASA from yeast capable of producing ASA from KLG. The present invention provides methods for the production of ASA as well as recombinant yeast capable of producing ASA from a carbon source.

10 Claims, 2 Drawing Sheets

OTHER PUBLICATIONS

*Grindley et al., "Conversion of Glucose to 2–Keto–L–Gulonate, an Intermediate in L–Acorbate Synthesis, by a Recombinant Strain of *Erwinia citreus, Applied and Environmental Microbiology*", Jul. 1988, p. 1770–1775.
*Haller et al., "Enzymatic Synthesis of L–Ascorbic Acid. 3. L–Galactono–Gamma–Lactone Oxidase from Yeasts", *Dechema Biotechnology Conferences*, DE, Weinheim, V. 4, Jan. 1, 1990, pp. 233–236, XP000646759 ISSN: 0934–3792.
*Heick et al., "Occurrence of ascorbic acid in the yeast *Lipomyces starkeyi*", *Canadian Journal of Biochemistry*, vol., 47, 1969, pp 752–753.
*Izumi et al., "NADH production from NAD using a formate Dehydrogenase System with Cells of a Methanol–Utilizing Bacterium", *J. Ferment. Technol.*, vol. 61, No. 2, p. 135–142, 1983.
*Kulbe et al., "Enzyme–Catalyzed Production of Mannitol and Gluconic Acid", *Annals of the New York Academy of Sciences*, vol. 506, 1987, pp 552–568.
*Loewus et al., "Conversion of D–Arabinose to D–erythroascorbic Acid and Oxalic Acid in *Sclerotinia Scierotiorum*," *Biochemical and Biophysical Res. Comm.*, V. 212:1 1995 pp. 196–203.
*Matsushita et al., "Membrane–Bound D–Gluconate Dehydrogenase from *Pseudomonas aeruginosa*", *J. Biochem*, vol. 85, No. 5, pp 1173–1181, 1979.
*McIntire et al., "Identification of the covalently bound flavins of D–gluconate dehydrogenases from *Pseudomonas aeruginosa* and of *Pseudomonas fluorescens* and 2–keto–D–gluconate de hydrogenase from *Gluconobacter melanogenus*", *Biochem.J*.(1985), 651–654.
*Murakawa, et al., "Biosynthesis of D–Erythroascorbic Acid by *Candida*," *Agric. Biol. Chem.*, 41(9), pp. 1799–1800, 1977.
*Neijssel et al., "Physiological Significance and Bioenergetic Aspects of Glucose Dehydrogenase", *Antonie Van Leeuwenhoek*, vol. 56, 51–61, 1989.

Nishikimi et al., "Occurrence in Yeast of L–Galactonolactone Oxidase Which is Similiar to Key Enzyme for Ascorbic Biosynthesis in Animals, L–Gulonolactone Oxidase", *Archives of Biochemistry and Biophysics*, vol. 191, No. 2, Dec., pp 479–486, 1978.
*Pachla et al. "Determination of Ascorbic Acid in Foodstuffs, Pharmaceuticals, and Body Fluids by Liquid Chromatography with Electrochemical Detection", *Analytical Chemistry*, vol. 48, No. 2, Feb. 1976, pp 364–367.
*Saito et al., "Cloning of Genes Coding for L–Sorbose Dehydrogenases from Gluconobacter oxydans and Microbial Production of 2–Keto–L–Gulonate, a Precursor of L–Ascorbic Acid, in a Recombinant G. oxydans Strain", *Applied and Environmental Microbiology*, Feb. 1977, p. 454–460.
Shinagawa et al., "2–Keto–D–gluconate Dehydrogenase from *Gluconobacter melanogenus*, Membrane–Bound, *Oxidation–Reduction Enzymes*", *Methods in Enzymology*, vol. 89, pp 194–198, 1991.
*Simons et al., "Aerobic 2–ketogluconate metabolism of *Klebsiella Pneumoniae* NCTC 418 grown in chemostat culture", *Journal of General Microbiology* (1991), 137, 1479–1483.
*Smith et al., Purification and characterization of glucose dehydrogenase from the thermoacidophilic archaebacterium Thermophlasma acidophilum, *Biochem. J.* (1989), 261, 973–977.
*Stoshane et al., "Fermentation of Glucose by *Acetobacter melanogenus*", *Biotechnology and Bioengineering*, vol. XIX, pp. 459, 465, 1977.
*Takahashi et al., "Ascorbic Acid Analogs as Indirect Products of *Serratia marcescens*,"*Agr. Biol. Chem.*, 40 (6),pp. 1255–1256, 1976.
Truesdell et al., "Pathways for Metabolism of Ketoaldonic Acids In an Erwinia sp.", *Journal of Bacteriology*, Nov. 1991, V. 173:21 pp. 6651–6656.

* cited by examiner

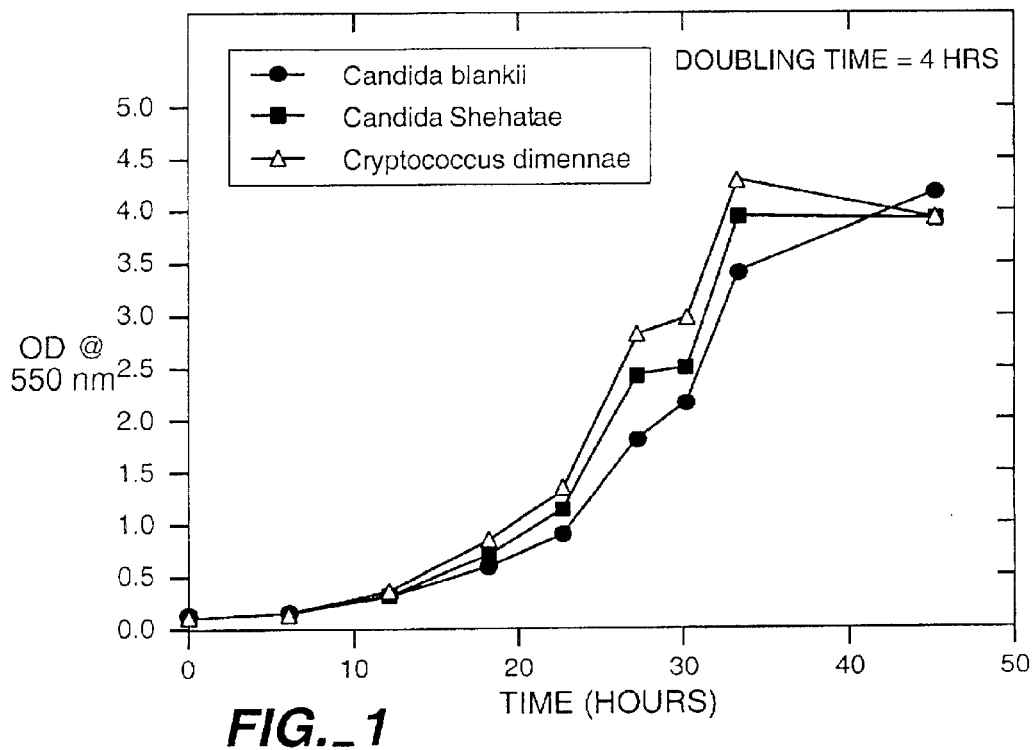
Growth of Selected Yeast batch cultures on 2KLG as a single carbon source (0.5%) in YNB at 23C & 250 rpm in Shake flasks
FIG._1
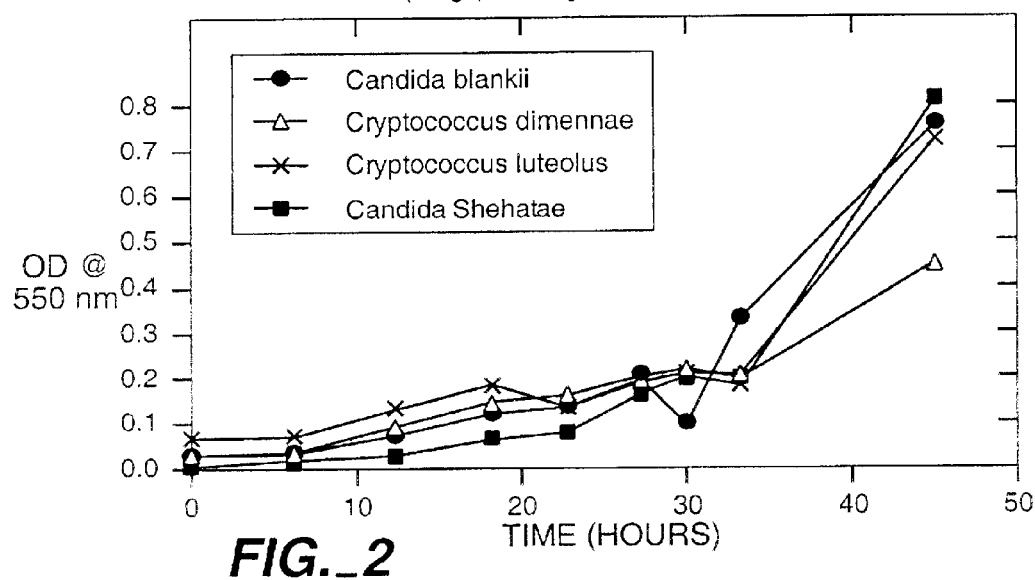
Growth of Selected Yeasts on Idonate Sodium salt (0.5%) in YNB medium (6.7g/l) as single carbon source at 23C & 250 rpm
FIG._2

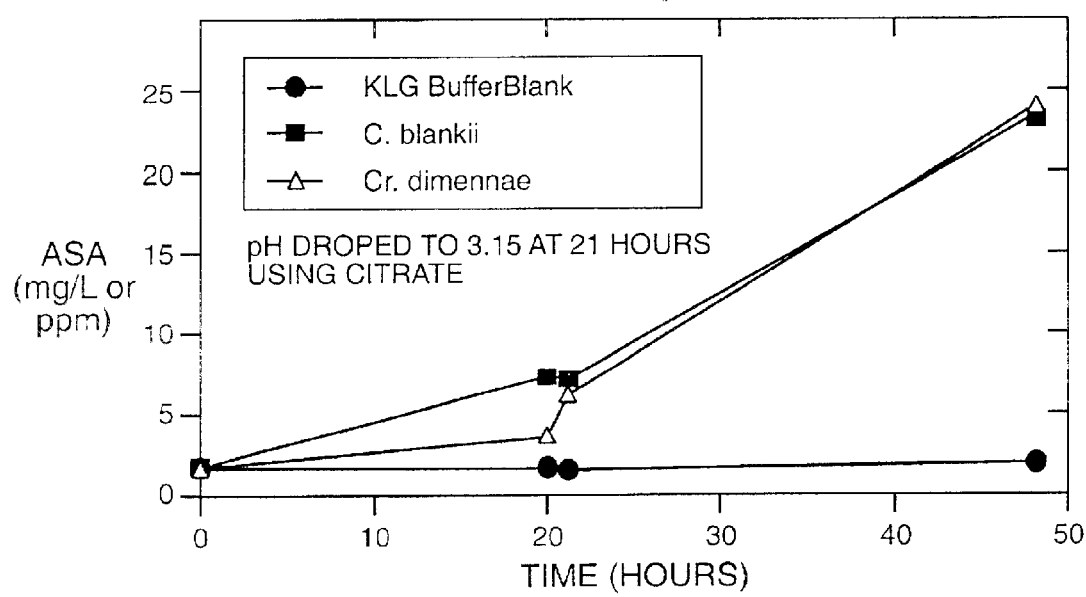
FIG._3

PRODUCTION OF ASCORBIC ACID

This is a divisional of application Ser. No. 09/205,874, filed Dec. 4, 1998, now U.S. Pat. No. 6,358,715.

FIELD OF THE INVENTION

The present invention relates to the field of molecular biology and the use of yeast for the production of ascorbic acid and ascorbic acid stereoisomers.

BACKGROUND OF THE INVENTION

L-Ascorbic acid (Vitamin C, ASA) finds use in the pharmaceutical and food industry as a vitamin and antioxidant. The synthesis of ASA has received considerable attention over many years due to its relatively large market volume and high value as a specialty chemical. The Reichstein-Grussner method, a chemical route from glucose to ASA, was first disclosed in 1934 (Helv. Chim. Acta 17:311–328). Lazarus et al. (1989, "Vitamin C: Bioconversion via a Recombinant DNA Approach", *Genetics and Molecular Biology of Industrial Microorganisms*, American Society for Microbiology, Washington D.C. Edited by C. L. Hershberger) disclosed a bioconversion method for production of an intermediate of ASA, 2-keto-L-gulonic acid (2-KLG, KLG) which can be chemically converted to ASA. Saito et al. (1997, Applied and Environmental Microbiology, 63: 454–460) report on the construction of an expression system for the production of 2-KLG from D-sorbitol.

The presence of ASA in yeasts has been reported (Heick et al. Can. J. Microbiol., 1972, 18, 597–600) and the conversion of L-galactonic substrates to ASA in *Candida* yeast has been disclosed (U.S. Pat. Nos. 4,595,659, issued Jun. 17, 1986 and U.S. Pat. No. 4,916,068, issued Apr. 10, 1990). Costamagna et al. (Can. J. Microbiol., 1986, 32, 756–758) disclose the results of a study on ASA utilization by some yeasts. This report discloses that species of *Cryptococcus* and *Candida* were able to grow on ASA as well as iso-ascorbic acid.

In spite of the scientific advances made in the production of ASA and its biocatalytic intermediates, there remains a need for methods for the production of ascorbic acid in order to supply the world's demand. The discovery of a method which utilizes a renewable carbon source to produce ascorbic acid would be particularly advantageous.

SUMMARY OF THE INVENTION

The present invention relates to the production of ascorbic acid or ascorbic acid stereoisomers in yeast. The present invention is based, in part, upon the unexpected discovery that multiple members of yeast which are able to grow on ascorbic acid or iso-ascorbic acid as a sole carbon source are capable of utilizing KLG as a sole carbon source to produce ascorbic acid.

Accordingly, the present invention provides methods for the production of ascorbic acid or an ascorbic acid stereoisomer from a yeast comprising the steps of obtaining a yeast capable of utilizing KLG to produce ascorbic acid or an ascorbic acid stereoisomer; and culturing the yeast in the presence of a carbon source under conditions suitable for the production of ascorbic acid or an ascorbic acid stereoisomer. ASA stereoisomers include D-ascorbic acid, D-araboascorbic acid and L-araboascorbic acid. The method may further comprise the step of recovering the ascorbic acid or ascorbic acid stereoisomer produced.

In one aspect of the present invention, the carbon source is a six carbon sugar acid. In another aspect of the present invention, the carbon source is a six carbon sugar and the yeast comprises either or both of a) a heterologous nucleic acid encoding an oxidative enzyme associated with the production of ascorbic acid or an ascorbic acid stereoisomer in said yeast and b) a heterologous nucleic acid encoding a reducing enzyme associated with the production of ascorbic acid or an ascorbic acid stereoisomer in said yeast.

In one embodiment of the present invention, the oxidative enzyme has a dehydrogenase activity. In another embodiment, the oxidative enzyme includes a glucose dehydrogenase activity, a gluconic acid dehydrogenase activity, a 2-keto-D-gluconic acid dehydrogenase activity, a galactose dehydrogenase activity, an L-sorbose dehydrogenase activity, an L-sorbosone-dehydrogenase activity, a 6 phosphogluconate kinase activity, a gluconate kinase activity, an L-idonic acid oxidase activity, and L-gulonic acid oxidase activity. In a further embodiment, the reducing enzyme is a reductase activity. In yet another embodiment, the reductase activity includes 2,5 DKG reductase activity, 2,3-DKG reductase, 5-keto reductase, 2-keto reductase and 2 ketogulonate reductase.

In one embodiment, the six carbon sugar acid includes 2-keto-L-gulonic acid, idonic acid, gluconic acid, 6-phosphogluconate, 2-keto-D-gluconic acid, 5-keto-D-gluconic acid, 2-ketogluconate-6-phosphate, 2, 5-diketo-L-gluconic acid, 2,3-L-diketogulonic acid, dehydroascorbic acid, erythroascorbic acid and D-mannonic acid. In another embodiment, the six carbon sugar includes glucose, gulose, sorbose, fructose, idose, galactose and mannose all in either D or L form.

In one embodiment of the present invention, the yeast is a member of the Imperfect yeast group. In another embodiment, the yeast is a member of the family *Cryptococcaceae*. In yet another embodiment, the yeast is *Candida* or *Cryptococcus*. In a further embodiment, the yeast is *Candida blankii* or *Cryptococcus dimennae*.

In a preferred embodiment of the present invention, the yeast is *Candida blankii* or *Cryptococcus dimennae*, said carbon source comprises glucose, and the yeast comprises at least one of a heterologous oxidative enzyme and a heterologous 2,5-DKG reductase activity. In another preferred embodiment, the yeast is *Candida blankii* or *Cryptococcus dimennae* and said carbon source comprises D-sorbitol, L-sorbose or L-sorbosone, and the yeast comprises at least one of a D-sorbitol dehydrogenase activity, an L-sorbosone dehydrogenase activity, L-sorbose dehydrogenase activity and a galactose dehydrogenase activity.

In a preferred embodiment, the carbon source is glucose and the yeast comprises heterologous nucleic acid encoding at least one of (a) a glucose dehydrogenase (GDH) activity; (b) a gluconic acid dehydrogenase (GADH) activity; (c) a 2-keto-D-gluconic acid dehydrogenase (2-KDGDH) activity; and (d) a 2,5-diketo-D-gluconic acid reductase (2,5-DKGR) activity provided that if the yeast comprises heterologous nucleic acid for less than all of (a)–(d), then the yeast comprises endogenous nucleic acid such that the yeast comprises nucleic acid for each of (a)–(d) and is capable of converting glucose to ASA via the intermediate KLG.

The present invention also provides recombinant yeast capable of utilizing KLG to produce ascorbic acid or an ascorbic acid stereoisomer comprising either or both of a) a heterologous nucleic acid encoding an oxidative enzyme associated with the production of ascorbic acid or an ascorbic acid stereoisomer in said yeast and b) a heterologous nucleic acid encoding a reducing enzyme associated with the production of ascorbic acid or an ascorbic acid stereoisomer in said yeast.

In a preferred embodiment, the yeast is a member of the Imperfect Yeast group. In another preferred embodiment, the yeast is a member of the family *Cryptococcaceae*. In yet another preferred embodiment, the yeast is selected from members of the genera consisting of *Candida* and *Cryptococcus*, including *Candida blankii* and *Cryptococcus dimennae*.

The present invention also encompasses a method for producing a recombinant yeast capable of utilizing a six carbon sugar to produce ASA or an ASA stereoisomer comprising the steps of obtaining a yeast capable of utilizing KLG to produce ASA or an ASA stereoisomer and introducing at least either or both of a) a heterologous nucleic acid encoding an oxidative enzyme associated with the production of ascorbic acid or an ascorbic acid stereoisomer in said yeast and b) a heterologous nucleic acid encoding a reducing enzyme associated with the production of ascorbic acid or an ascorbic acid stereoisomer in said yeast. In one embodiment of the method the yeast is a member of the Imperfect yeast group. In another embodiment, the yeast is a member of the family *Cryptococcaceae*, including *Candida* and *Cryptococcus*. In yet another embodiment, the yeast is *Candida blankii*. In a further embodiment, the yeast is *Cryptococcus dimennae*. In yet another embodiment, the yeast is *Candida blankii* or *Cryptococcus dimennae*, said carbon source comprises glucose and said yeast comprises a heterologous oxidative enzyme activity and a 2,5-DKGreductase activity. In an additional embodiment, the yeast is *Candida blankii* or *Cryptococcus dimennae*, said carbon source comprises D-sorbitol, L-sorbose or L-sorbosone, and said yeast comprises at least one of a D-sorbitol dehydrogenase activity, an L-sorbosone dehydrogenase activity, an L-sorbose dehydrogenase activity or a galactose dehydrogenase activity.

BRIEF DESCRIPTION OF THE DRAWINGS

FIG. 1 illustrates the growth of *Candida blankii, Candida shahatae* and *Cryptococcus dimmnae* on 2KLG as a single carbon source in yeast nitrogen base.

FIG. 2 illustrates the growth of *Candida blankii, Candida shahatae, Cryptococcus dimmnae* and *Cryptococcus luteolus* on idonate sodium salt in yeast nitrogen base.

FIG. 3 illustrates the determination of ASA content in the supernatant of *Candida blankii* and *Cryptococcus dimennae* from a whole cell reaction mixture using ascorbate oxidase assay.

DETAILED DESCRIPTION

Definitions

As used herein the term "ascorbic acid" is the name recognized by the IUPAC-IUB Commission on Biochemical Nomenclature for Vitamin C. Other names are L-ascorbic acid, L-xyloascorbic acid and L-threo-hex-2-enoic acid γ lactone. The pure vitamin is $C_6H_8O_6$ and has molecular weight 176.13. Four stereoisomers of ascorbic acid are possible: L-ascorbic acid, D-araboascorbic acid (erythorbic acid), which shows vitamin C activity, L-araboascorbic acid, and D-xyloascorbic acid. Ascorbic acid intermediates or "pathway intermediates" are those biochemicals capable of being converted to ASA via enzymatic or chemical means and include, but are not limited to, gluconic acid, 2-keto-D-gluconic acid, 2,5-diketo-D-gluconic acid, 2-keto-L-gulonic acid, idonic acid, gluconic acid, sorbitol, sorbose, sorbosone, and sorbose diacetone.

The phrase "capable of utilizing KLG to produce ascorbic acid or an ascorbic acid stereoisomer" when referring to a yeast means a yeast which is able to produce ascorbic acid from KLG through any means including biocatalytic conversion and chemical conversion.

It is well understood in the art that the acidic derivatives of saccharides, may exist in a variety of ionization states depending upon their surrounding media, if in solution, or out of solution from which they are prepared if in solid form. The use of a term, such as, for example, idonic acid, to designate such molecules is intended to include all ionization states of the organic molecule referred to. Thus, for example, "idonic acid", its cyclized form "idonolactone", and "idonate" refer to the same organic moiety, and are not intended to specify particular ionization states or chemical forms.

As used herein, the term "recombinant" refers to a yeast that contains nucleic acid not naturally occurring in the organism and/or to yeast having additional copies of endogenous nucleic acid recombinantly introduced. The term "heterologous" as used herein refers to nucleic acid or amino acid sequences not naturally occurring in the yeast. As used herein, the term "endogenous" refers to a nucleic acid naturally occurring in the yeast. A recombinant host may also have mutations and/or deletions in naturally occurring nucleic acid such that the protein encoded by the nucleic acid is not produced.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof.

The phrase "oxidative enzyme" as used herein refers to an enzyme or enzyme system which can catalyze conversion of a substrate of a given oxidation state to a product of a higher oxidation state than substrate. The phrase "reducing enzyme" refers to an enzyme or enzyme system which can catalyze conversion of a substrate of a given oxidation state to a product of a lower oxidation state than substrate. Oxidative enzymes associated with the biocatalysis of a 6 carbon sugar to pathway intermediates of ASA include among others D-glucose dehydrogenase, D-gluconate dehydrogenase and 2-keto-D-gluconate dehydrogenase as well as L-sorbitol dehydrogenase activity, L-sorbose dehydrogenase and L-sorbosone dehydrogenase activity. Reductive enzymes associated with the biocatalysis of pathway intermediates of ASA into desired end-products include among others 2,5-diketo-D-gluconate reductase (DKGR), 2-keto reductase (2-KR) and 5-keto reductase (5-KR). Such enzymes include those produced naturally by the host yeast or those introduced via recombinant means.

As used herein the term "6 carbon sugar acid" specifically excludes L-galactonic substrates and includes but is not limited to 2-keto-L-gulonic acid, idonic acid, gluconic acid, 6-phosphogluconate, 2-keto-D-gluconic acid, 5-keto-D-gluconic acid, 2-ketogluconatephosphate, 2,5-diketo-L-gulonic acid, 2,3-L-diketogulonic acid, dehydroascorbic acid, erythroascorbic acid and D-mannonic acid.

As used herein the term "6 carbon sugar" includes but is not limited to glucose, gulose, sorbose, fructose, idose, galactose and mannose all in either D or L form.

The terms "isolated" or "purified" as used herein refer to a nucleic acid or protein or peptide that is removed from at least one component with which it is naturally associated. In the present invention, an isolated nucleic acid can include a vector comprising the nucleic acid. Purified as used herein to describe a carbon source derived from a fermentative process refers to removing that carbon source from at least one component with which it is naturally associated in the fermentation culture.

DETAILED DESCRIPTION
Production of ASA in Yeast

The present invention relates to the production of ASA or ASA stereoisomers, e.g., erythorbic acid, in yeast that are capable of utilizing KLG as a sole carbon source to produce ASA. The present invention specifically excludes a method for producing ASA in yeast which produce ASA via the L-galactonolactone oxidase pathway. Yeasts are described in N. J. W. Kreger-van Rij, in "The Yeasts", Vol. 1 of Biology of Yeasts, Ch. 2, Eds. A. H. Rose & J. S. Harrison, 1987, Academic Press, London. Yeasts belonging to the genera Imperfect yeasts are generally characterized as not forming ascospores and basidiospores. Because ASA is oxygen sensitive, it is preferred that the yeast be capable of growing anaerobically in order to reduce oxidation of the ASA produced. The present invention also encompasses methods of producing ASA using yeast that are cultured under aerobic conditions as long as reducing agents like dithioetrythretol, glutathione, metal chelators like EDTA, stabilizers like metaphosphoric acid, amino acids, glycols, sugars, oxalic acid, trichloroacetic acid, 8-hydroxyquinoline are present in the ASA environment (D. W. Bradley, G. Emery, and J. E. Maynard, Clin. Chim. Acta 4, 47–52 (1973).

Yeasts which may be used in the present invention include but are not limited to those listed herein and are exemplified by the deposit designation following the listing: *Candida blankii* CBS1898, ATCC 18735; *C. curvata* CBS570; *C. humicola*; *C. incommunis* ATCC22971; *C. salmanticensis* ATCC16042; *C.* sp. ATCC 28528, ATCC 20473; *Cryptococcus albidus* CBS4192; *Cr. dimennae* CBS5770; *Cr. heveanensis* CBS140; *Cr. kuetzingii* UCD68-196; *Cr. luteolus* CBS953; *Cr. skinneri* UCD60-82 CBS5029; *Cr. terreus* CBS1895, CBS6293 CCY17-8-5; *Cr. uiguttulatus* CBS1730; *Cr. laurentii* CCY 17-3-2, CCY17-3-6, ATCC32044; *Cr. neoformans* ATCC32045; *Cr. podzolicus* CCY17-20-1; *Trichosporon cutaneum* UCD54-169 CCY30-5-4; *T. beigelii* NRRLY-1490; *T. pullulans* ATCC10677; *Aureobasidium pullulans* DBV A9, A10, A62, A77 A84; *Hansenula capsulata* DBV 3164, ATCC24204; *Lipomyces starkeyi* UCD 51-55, CBS1809; *L. lipofer* NRRL Y-1351, *Phaffia rhodozyma* ATCC24201, *Rhodotorula mucilaginosa* NRC 211003; *Saccharomyces uvarum* ATCC9373, ATCC 9080; *Saccharomycopsis fibuligera* ATCC2082; *Schwanniomyces occidentalis* NRC2782, NRC2783; and *Torulopsis ernobii* ATCC20000. In a preferred embodiment, the yeast is a member of the Imperfect yeast group. A preferred family of Imperfect yeast to use in methods for producing ASA is the family *Cryptococcaceae*. Preferred genera of *Cryptococcaceae* are selected from the group consisting of Candida and Cryptococcus.

As demonstrated in the Examples, *Candida blankii* and *Cryptococcus dimennae* were able to produce ASA over background levels when grown on KLG as a sole carbon source whereas *Candida shahatae*, while being able to grow on KLG as a sole carbon source, was unable to produce ASA. The illustrative Examples disclose the use of *Candida shahatae* ATCC accession number 34887, *Candida blankii* ATCC accession number 18735, *Cryptococcus dimennae* ATCC accession number 22024 and *Cryptococcus luteolus* ATCC accession number 32044. The present invention encompasses mutants, derivatives and progeny of known species of yeast, and in particular, mutants and derivatives of known species belonging to the genera *Cryptococcaceae*, e.g., those belonging to *Candida* and *Cryptococcus*, as long as the mutant, derivative or progeny is able to utilize KLG as a sole carbon source to produce ASA.

The present invention encompasses methods for producing ASA or ASA stereoisomers in yeast wherein the yeast is naturally occurring, i.e., is not genetically engineered, as well as wherein the yeast is recombinant and comprises heterologous nucleic acid encoding oxidative and/or reducing enzymes that are associated with conversion of a carbon source to KLG in the yeast. In the present invention, the carbon source, such as a 6 carbon sugar acid, may be a product of a separate fermentative process that is fed into a yeast culture, such as KLG made by the method disclosed by Lazarus et al (J. Bact. 1991, 173, 6651–61) or by the method disclosed in Saito et al. (1997, Applied and Environmental Microbiology, 63: 454–460). The carbon source derived from a separate fermentative process may be purified prior to use in a method for producing ASA or ASA sterioisomers or used directly from the fermentation process. The carbon source may also be derived from chemical means.

In another embodiment of the present invention, the yeast is genetically engineered to comprise either or both of a heterologous oxidative enzyme or a heterologous reducing enzyme associated with the conversion of a carbon source to KLG in the yeast thereby providing a single organism that is capable of converting a carbon source, such as glucose or other 6 carbon sugar, to ascorbic acid via KLG as an intermediate. The recombinant yeast host may comprise multiple heterologous oxidative enzymes and/or multiple heterologous reducing enzymes in order to produce ascorbic acid from a 6 carbon sugar or 6 carbon sugar acid.

In one preferred embodiment, the carbon source is glucose and the recombinant yeast comprises heterologous nucleic acid encoding at least one of (a) a glucose dehydrogenase (GDH); (b) a gluconic acid dehydrogenase (GADH); (c) a 2-keto-D-gluconic acid dehydrogenase (2-KDGDH); and (d) a 2,5-diketo-D-gluconic acid reductase (2,5-DGKR) provided that if the yeast comprises heterologous nucleic acid for less than all of (a)–(d), then the yeast comprises endogenous nucleic acid such that the yeast comprises nucleic acid for each of (a)–(d) and is capable of converting glucose to ASA via the intermediate KLG. As will be readily understood by the skilled artisan, oxidation and reducing reactions involved in the conversion of a carbon substrate to ASA may require co-factors to be added to the yeast cultures. For example, 2,5-DGKR described in U.S. Pat. No. 5,032,514 issued Jul. 16, 1991, has a requirement for NADPH. Other examples of co-factors necessary in enzymatic reactions include, but are not limited to, ATP, NAD+, NADP+, NADH, NADPH and coenzyme A. The yeast may also have deletions or mutations of endogenous oxidative and/or reducing enzymes that interfere with the desired path of carbon flow.

In another embodiment of the present invention, the carbon source is sorbitol and the recombinant yeast comprises heterologous nucleic acid encoding at least one of (a) D-sorbitol dehydrogenase (SLDH); (b) L-sorbose dehydrogenase; and (c) L-sorbosome dehydrogense provided that if the yeast comprises heterologous nucleic acid for less than all of (a)–(c), then the yeast comprises endogenous nucleic acid such that the yeast comprises nucleic acid for each of (a)–(c) and is capable of converting sorbitol to ASA via the intermediate 2KLG.

Sources for nucleic acid encoding oxidative or reducing enzymes include the following:

| ENZYME | CITATION |
| --- | --- |
| glucose dehydrogenase | Smith et al. 1989, Biochem. J. 261:973; Neijssel et al. 1989, Antonie Van Leauvenhoek 56(1):51–61 |
| gluconic acid dehydrogenase | Matsushita et al. 1979, J. Biochem. 85:1173; Kulbe et al. 1987, Ann. N.Y. Acad Sci 506:552 |
| 2-keto-D-gluconic acid dehydrogenase | Stroshane 1977 Biotechnol. BioEng 19(4) 459 |
| 2-keto gluconate reductase | J. Gen. Microbiol. 1991, 137:1479 |
| 2,5-diketo-D-gluconic acid reductase | U.S. Pat. Nos.: 5,795,761; 5,376,544; 5,583,025; 4,757,012; 4,758,514; 5,008,193; 5,004,690; 5,032,514 |
| L-sorbose dehydrogenase; L-sorbosone-dehydrogenase; 1997, and L-sorbitol dehydrogenase | Saito et al. Applied and Envionmental Microbiology, 63:454 |

Construction of Recombinant Yeast

Recombinant yeast containing the nucleic acid(s) necessary to produce ASA from a carbon source may be constructed using techniques well known in the art. Molecular biology techniques are disclosed in Sambrook et al., Molecular Biology Cloning: A Laboratory Manual, Second Edition (1989) Cold Spring Harbor Laboratory Press, Cold Spring Harbor, N.Y. (1989). Genes encoding oxidative enzymes and reducing enzymes associated with ASA production can be isolated from native hosts as described infra or produced by chemical means. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (PCR) (U.S. Pat. No. 4,683,202) to obtain amounts of nucleic acid suitable for transformation using appropriate vectors. A variety of vectors and transformation and expression cassettes suitable for the cloning, transformation and expression in yeast of nucleic acid encoding oxidative and reducing enzymes associated with ASA production are known by those of skill in the art. Protocols for obtaining and using such vectors are known to those in the art. (Sambrook et al., Molecular Cloning: A Laboratory Manual—volumes 1, 2, 3 (Cold Spring Harbor Laboratory, Cold Spring Harbor, N.Y., (1989)).

Typically, the vector or cassette contains sequences directing transcription and translation of the nucleic acid, a selectable marker, and sequences allowing autonomous replication or chromosomal integration. Suitable vectors comprise a region 5' of the gene which harbors transcriptional initiation controls and a region 3' of the DNA fragment which controls transcriptional termination. These control regions may be derived from genes homologous or heterologous to the yeast as long as the control region selected is able to function in the yeast.

Initiation control regions or promoters, which are useful to drive expression of the oxidative or reducing enzymes in yeast are known to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI. Nucleic acid encoding the oxidative or reducing enzymes are linked operably through initiation codons to selected expression control regions for effective expression of the oxidative or reducing enzymes.

Once suitable cassettes are constructed they are used to transform yeast and the yeast are screened for the ability to produce ASA from an appropriate carbon source. For example, in one embodiment, the yeast is transformed with nucleic acid encoding either one or both of a dehydrogenase activity and a reductase activity and the transformed yeast are screened for their ability to produce ASA from a six carbon sugar, such as glucose or a six carbon sugar acid, such as KLG. Detection of ASA Methods for detection of ASA and ASA sterioisomers include the use of redox-titration with 2,6 dichloroindophenol (Burton et al. 1979, J. Assoc. Pub. Analysts 17:105); high-performance liquid chromatography (HPLC) using anion exchange (J. Chrom. 1980, 196:163); and electroredox procedures (Pachia, 1976, Anal. Chem. 48:364). Enzymatic procedures involving the use of ascorbic acid oxidase may also be employed.

In the present invention, the detection of ASA was accomplished by HPLC, Colorometric Ascorbate oxidase assay as used herein and GC-mass spectrophotometry. The skilled artisan will be well aware of controls to be applied in utilizing these detection methods. Because a chemical equilibria exists between KLG and ASA (i.e., KLG contains background levels of ASA), for the use of HPLC UV detection of ascorbic acid, the elution profile of the substrate KLG was recorded and used as a control. For the ascorbate oxidase assay, a control of blank runs without sample and enzyme were run. For GCMS analysis, derivatizing agent and the substrate KLG was analysed as a control.

It is also desirable to have a screening method for the detection of yeast which are capable of producing ASA from a carbon source. A method for screening for yeast capable of producing ASA comprising the steps of obtaining yeast capable of growing on ascorbic acid or ascorbic acid stereoisomer, culturing said yeast in the presence of KLG under conditions suitable for the production of ascorbic acid or an ascorbic acid stereoisomer; and assaying said yeast culture for the production of ascorbic acid or an ascorbic acid stereoisomer.

Fermentation and Purification

Media and Carbon Substrates

Naturally occurring yeast or recombinant yeast capable of utilizing KLG to produce ASA are subjected to large scale fermentation in the presence of a suitable carbon source and the ASA is recovered. Suitable carbon sources include six carbon sugars or six carbon sugar acids. The source of carbon utilized in growing the yeast disclosed herein will only be limited by the requirements of the host organism. For example, naturally occurring yeast may be grown in the presence of a six carbon sugar acid, e.g., KLG, whereas recombinant yeast which have been genetically engineered to contain nucleic acid encoding either one or both of dehydrogenase and reductase may be grown in the presence of a six carbon sugar, e.g., as glucose. In addition to an appropriate carbon source, fermentation media must contain suitable minerals, salts, cofactors, buffers and other components, known to those skilled in the art, suitable for the growth of the cultures and production of ASA. Methods for media and culture conditions suitable for growing yeast are described in Costamagna et al., 1986, Can. J. Microbiology, 32:756–758.

The yeast may be grown under aerobic or anaerobic conditions. Because ASA is oxygen sensitive, growing the ASA producing yeast aerobically will reduce oxidation of the ASA produced. Alternatively, if the yeast are grown under aerobic conditions, it is preferred that reducing agents, e.g., dithiothreitol, glutathione, metal chelators like EDTA, stabilizers like metaphosphoric acid, amino acids, glycols, sugars, oxalic acid, trichloroacetic acid, 8-hydroxyquinoline are present in the ASA environment. The present invention encompasses batch or continuous fermentation and the process of producing ASA may proceed in one or two fermentors. For example, if the yeast is genetically engineered to comprise a pathway from a six carbon sugar, such as glucose for example, to a six carbon sugar acid, such as KLG, ASA production could proceed in one fermentor using the recombinant yeast as a host. If the yeast is naturally occurring and ASA is produced in the yeast from a six carbon sugar acid, e.g., KLG, the ASA production may proceed in two fermentors, one for producing KLG as described in U.S. Pat. No. 5,032,514 or by Saito et al. supra, and one for producing ASA from KLG in yeast.

A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a batch fermentation is "batch" with respect to the addition of the carbon source and attempts are often made at controlling factors such as pH and oxygen concentration. The metabolite and biomass compositions of the batch system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch fermentation system which is also suitable in the present invention. In this variation of a typical batch system, the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Brock, supra.

It is also contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

The methods of the present invention may be practiced using either batch, fed-batch or continuous processes. After fermentation, the ASA produced may be recovered from the fermentation broth by a variety of methods including ion exchange resins, absorption or ion retardation resins, activated carbon, concentration-crystallization, etc.

Various aspects of the present invention will be further described with respect to the following specific examples, which are not intended to limit the scope of the present invention.

EXAMPLES

The following description of Materials and Methods applies to Examples 1-III.
Materials and Methods
Culture Conditions Yeast were grown on cultured on Difco yeast nitrogen base (YNB) 6.7 g/l with initial growth on 2% glucose followed by transfer to 0.5% (w/v) sole carbon source of L-ASA and then 2-KLG or L-idonate 20.8 mM. The yeast were cultured in 50 ml YNB medium at 22° C., pH 5.5 for a 48 hours cycle at a agitation speed of 250 rpm in a shake-flask.

HPLC: HPLC elution of ascorbate and other keto sugar acids were performed using Dionex IonPac AS10 analytical column with a guard column. Isocratic elution using 40 mM acetate pH 4.86 eluent was employed for obtaining good retention time separation between substrate KLG and product ascorbate (>5 mins). Ascorbate was detected (>100 ppb) using UV detector between wavelength 245–270 nm, whereas KLG was detected using refractive index detector. HPLC system used for the study is a HP-Alliance machine, equipped with Millenium software package used for peak-area integration calculation. Calibration curve for ascorbate quantification was generated between (100 ppb -100ppm).

GC-MS: Ascorbate identification using GC-MS were performed using a published procedure (J. C. Deutsch and J. Fred Kolhouse, Anal. Chem., 1993, 65, 321–326). GC work was performed on a HP equipment 5890 using a 15 meter by 0.25 mm Supelco SPB-1 fused-silica capillary column. Ascorbate derivatization was done using N-methyl-N-(tert-butyldimethylsilyl)trifluoroacetamide and acetonitrile following the method reported in the above reference. Standard ascorbate retention time obtained under our experimental conditions was 8.75 minutes. Characteristic mass fragmentation pattern of m/z 575, 531, 443, 343 were detected in the spectra obtained for both standard and unknown samples.

Ascorbate Oxidase Assay: Ascorbate oxidase assay was performed using L-ascorbic acid determination kit (cat. No. 409677) procured from Boehringer Mannheim and following the protocol provided with. The kit contained ascorbate oxidase enzyme and a detection/quantitation (578 nm) using a coupled dye system of MTT and PMS (Beutler, H.-O. and Beinstingl, G, 1984, in methods of enzymatic analysis (Bergmeyer, H. U. Ed.) $3^{rd}$ ed., vol. 7, pp. 376–385, Verlag Chemie, Weinheim, Deerfield, Beach/Florida., Basel.

Controls and blanks: 0.5% 2-KLG solution contains~2 ppm Ascorbate at pH 6.1. A buffer only control reaction containing KLG was run alongside each experiment as a control reaction along with a yeast containing reaction mixture during the time course of the whole cell KLG to ASA conversion experiment. In another control, yeast cells were heat-killed and then incubated with KLG to make sure no KLG to ASA transformation is detected under these conditions. Ascorbate peak detected by HPLC analysis was further confirmed by reaction of the sample with ascorbate oxidase and thus disappearance of the peak in the chromatogram due to ascorbate degradation by the ascorbic oxidase.

Example I

This Example illustrates that the yeast *Candida blankii* is capable of utilizing KLG or idonate as a sole carbon source for growth. This Example also shows the production of ascorbic acid by *Candida blankii* when grown in the presence of KLG as a sole carbon source.

*Candida blankii* having ATCC accession number 18735 was cultured as described in the materials and methods sections. The whole-cell KLG to ASA reaction was performed as described below. About 3 gram of wet cells were collected from a 500 ml, 48 hour growth culture by centrifugation at 4 degrees C. and 9000 rpm. Cells were washed with cold 200 mM phosphate buffer at pH 6.1 containing 0.5 mM EDTA. Cells were then resuspended in the same buffer containing 0.5% KLG (10 ml). Three ml of this reaction mixture was withdrawn and boiled in a microwave for two minutes. Both reaction mixtures were then set to 30 degrees C. in a rotary incubator for the whole-cell ASA production. 1.5 ml sample for time zero were withdrawn, centrifuged to remove the cell pellet and stored at −20 degrees C. The supernatant was filtered through a 0.2 u filter and subjected to HPLC analysis followed by ascorbate oxidase and GCMS analysis as described above. The same sample withdrawal and work-up method was used for the 2, 4 and 20 hour time points for the live-cell reaction and the 20 hour sample for the heat-killed reaction mixture (Table 1). Heat killed samples did not have background levels of ASA and did not produce ASA.

After the 20 hour sample withdrawal, the pH of the reaction mixture was lowered by three pH units to pH 3.15 by using citrate-phosphate buffer. A sample was withdrawn and analyzed at 21 hours to mark zero time for this condition change. The reaction was allowed to continue overnight. After another 24 hr. period, the final sample was taken. A parallel KLG blank control reaction without cells was run at both pH values to observe background production of ASA from KLG (see Table 1, FIG. 3).

As can be seen from Table 1 and FIG. 3, when growing *C. blankii* in the whole cell culture using KLG as a sole substrate, the presence of ASA was confirmed in the reaction medium. The concentration of the ASA present in the reaction mixture exceeded by 3 fold the background levels. By lowering the pH of the reaction mixture to pH 3, another 3 fold increase in ASA levels was observed. Lowering the pH had the effect of stabilizing the ASA as well as favoring the chemical thermodynamics toward ASA production.

Example II

This Example illustrates that *Cryptococcus dimennae* is able to utilize KLG or idonate as a sole carbon source for growth This Example also shows the production of ascorbic acid by *Cryptococcus dimennae* when grown in the presence of KLG as a sole carbon source.

*Cryptococcus dimennae* having ATCC accession number 22024 was cultured as described in the materials and methods sections. The whole-cell KLG to ASA reaction was performed as described in Example I.

As can be seen from Table 1 and FIG. 3, when growing in the whole cell *Cryptococcus dimennae* culture using KLG as a sole substrate, the presence of ASA was confirmed in the reaction medium. The concentration of the ASA present in the reaction mixture exceeded by 2 fold the background levels.

Example III

This Example illustrates that *Candida shahatae* is capable of using KLG as a sole carbon source, but is not able to produce ASA. The whole cell KLG to ASA reaction was performed as described in Example 1. As can be seen from FIG. 1, *Candida shahatae* is not able to produce ASA from KLG under these conditions.

TABLE 1

HPLC Results AU/Area and mg/L ASA Concentration in the Samples

| Samples | AU/Area @ 266 nm | | | mg/L Ascorbic Acid Conc. | | |
|---|---|---|---|---|---|---|
| | Time 0 hr | Time 4 hr | Time 20 hr | Time 0 hr | Time 4 hr | Time 20 hr |
| 2KLG Buffer Blank | 259831 | 280706 | 264840 | 1.9 | 2.1 | 1.9 |
| *Candida blankii* | 314059 | 240613 | 905162 | 2.3 | 1.8 | 6.6 |
| *Candida shahatae* | 204867 | 205323 | 270663 | 1.5 | 1.5 | 1.9 |
| *Cryptoc. Dimennae* | 224203 | 223112 | 522325 | 1.6 | 1.6 | 3.8 |

What is claimed is:

1. A recombinant yeast comprising either one or both at
    a) a heterologous nucleic acid encoding a glucose dehydrogenase, a gluconic acid dehydrogenase or a 2-keto-D-gluconic acid dehydrogenase, and
    b) a heterologous nucleic acid encoding a 25-diketo-L-gluconic acid (25-DKG) reductase, wherein the yeast is a member of the family *Cryptococcaceae* and is capable of utilizing 2-keto-L-gulonic acid (KLG) as a sole carbon source to produce ascorbic acid or an ascorbic acid stereoisomer.

2. The yeast of claim 1 wherein the yeast is a *Candida* or *Cryptococcus*.

3. The yeast of claim 2 wherein the yeast is *Candida blankii*.

4. The yeast of claim 2 wherein the yeast is *Cryptococcus dimennae*.

5. A recombinant yeast comprising either one or both of
    a) a heterologous nucleic acid encoding a glucose dehydrogenase and
    b) a heterologous nucleic acid encoding a 2,5-diketo-L-gluoonio acid (2,5-DKG) reductase
wherein said yeast is *Candida blankii* or *Cryptococcus dimennae* capable of utilizing 2-keto-L-gulonic acid (KLG) as a carbon source to produce ascorbic acid or an ascorbic acid stereoisomer and capable of converting glucose to KLG and utilizing the KLG to produce ascorbic acid or an ascorbic acid stereoisomer.

6. The recombinant yeast of claim 5 wherein said yeast is *Candida blankii*.

7. The recombinant yeast of claim 5 wherein said yeast is *Cryptococcus dimennae*.

8. A recombinant yeast capable of utilizing 2-keto-L-gulonic acid (KLG) as a carbon source to produce ascorbic add or an ascorbic acid stereoisomer, said yeast comprising at least one heterologous nucleic acid encoding a L-sorbose dehydrogenase, a D-sorbitol dehydrogenase, a L-sorbosone dehydrogenase or a galactose dehydrogenase, wherein said yeast is *Candida blankii* or *Cryptococcus dimennae* and is capable of converting sorbitol to KLG and then utilizing the KLG to produce ascorbic acid or an ascorbic acid stereoisomer.

9. The recombinant yeast of claim 8 wherein said yeast is *Candida blankii*.

10. The recombinant yeast of claim 8 wherein said yeast is *Cryptococcus dimennae*.

* * * * *